& Granger

United States Patent [19]
Gaussens et al.

[11] Patent Number: 4,747,990
[45] Date of Patent: May 31, 1988

[54] PROCESS OF MAKING A HIGH MOLECULAR WEIGHT POLYOLEFIN PART

[75] Inventors: Gilbert Gaussens, Meudon; Jean M. Haudin; Bernard Monasse, both of Antibes, all of France

[73] Assignees: CIE Oris Industrie S.A.; Association pour la Recherche et le Developpement des Methodes et Processus Industriels (A.R.M.I.N.E.S.), both of Paris, France

[21] Appl. No.: 836,976

[22] Filed: Mar. 6, 1986

[30] Foreign Application Priority Data

Mar. 12, 1985 [FR] France ............................ 85 03591

[51] Int. Cl.$^4$ .................... B29C 43/16; B29C 43/52
[52] U.S. Cl. ................................. 264/322; 264/325; 264/331.17; 264/337; 623/19; 623/20; 623/22
[58] Field of Search ............... 264/294, 320, 322, 325, 264/331.17, 337, DIG. 66; 526/352; 528/950; 623/18, 19, 20, 22, 23

[56] References Cited

U.S. PATENT DOCUMENTS

| | | | |
|---|---|---|---|
| 3,124,623 | 3/1964 | Slawson | 264/322 X |
| 3,373,238 | 3/1968 | Powers, Jr. et al. | 264/320 X |
| 3,825,648 | 7/1974 | Kulkarni | 264/322 |
| 4,055,862 | 11/1977 | Farling | 623/18 |
| 4,110,391 | 8/1978 | Berzen et al. | 264/120 |
| 4,195,368 | 4/1980 | Patrichi | 3/1.91 |
| 4,205,400 | 6/1980 | Shen et al. | 3/1.91 |
| 4,209,480 | 6/1980 | Homsy | 264/108 |
| 4,547,910 | 10/1985 | Roberts et al. | 623/18 |
| 4,587,163 | 5/1986 | Zachariades | 264/331.17 X |

FOREIGN PATENT DOCUMENTS

| | | | |
|---|---|---|---|
| 2301810 | 7/1973 | Fed. Rep. of Germany | 623/22 |
| 2903366 | 7/1979 | Fed. Rep. of Germany | 623/22 |
| 2338690 | 8/1977 | France . | |
| 58-118749 | 7/1983 | Japan | 623/18 |

OTHER PUBLICATIONS

Werner, A. C. et al, "Forging High Molecular Weight Polyethylene", SPE Journal, vol. 24 (Dec. 1968), pp. 76–79.
Atlas of Limb Prosthetics, St. Louis, C. V. Mosby Company, 1981, pp. 59–62.
Modern Plastics International, vol. 13, No. 2, Feb. (1983), "Self-Reinforced Polyethylene has Potential for High-Precision Parts".
Modern Plastics International, Oct. 1981, pp. 38–39, G. Menges et al., "Self-Reinforcing Plastics: A New Approach to High-Performance Resins".

Primary Examiner—Jeffery Thurlow
Assistant Examiner—Leo B. Tentoni
Attorney, Agent, or Firm—Pearne, Gordon, McCoy & Granger

[57] ABSTRACT

The invention relates to a high molecular weight polyolefin part, particularly for an articular prosthesis and to its production process by shaping in a closed mould. This part, which has a friction surface, has a structure such that the polyolefin chains are oriented parallel to the friction surface, at least in the zone of the part located below or flush with said friction surface. This orientation is obtained during the shaping of the blank of the part in a closed mould having a metal belt, a hemispherical block and a mobile punch, as a result of the choice of shaping conditions, particularly the shaping temperature and the length/transverse dimension ratio of the blank.

10 Claims, 1 Drawing Sheet

PROCESS OF MAKING A HIGH MOLECULAR WEIGHT POLYOLEFIN PART

BACKGROUND OF THE INVENTION

The present invention relates to a high molecular weight polyolefin part, particularly for an articular prosthesis, which resists friction and creep, as well as to a process for producing said part by shaping, forming or forging in a closed die or mould.

More specifically it relates to parts for a high molecular weight polyolefin articular prosthesis, in which the chains of the polyolefin have a special orientation obtained during the shaping of the parts in the closed mould and which makes it possible to improve the creep and wear resistance of said parts. Articular prostheses, such as total prostheses of the hip are generally constituted by two parts having a hemispherical portion, which rub against one another. These two parts are on the one hand a femoral prosthesis with a joined or unjoined head and tail, the latter being made from a metallic alloy, e.g. stainless steel, cobalt-chromium-molybdenum alloy or a titanium alloy, whilst the head is metallic or ceramic, e.g. of fritted alumina and on the other hand a cotyloid or cup-shaped prosthesis fixed to the pelvis by means of a polymer cement, e.g. of polymethyl methacrylate. The cup-shaped prosthesis can be made from a ceramic material such as fritted alumina, but it is usually made from very high molecular weight polyethylene. Thus, ceramics are fragile materials, which at present limits there development in such prostheses. Therefore, most existing prostheses have a high molecular weight polyethylene cup-shaped prosthesis, their life being estimated as approximately 12 years. The latter does not appear to be limited by the biocompatibility of the material, and instead is due to creep and wear phenomena with respect to the cup-shaped prosthesis. Research is being continued with aim of attempting to increase the life of articular prostheses. To this end, consideration has been given to either changing the materials forming the prosthesis, or at attempting to improve the mechanical properties of existing prostheses. The second solution would appear to be more interesting, because it avoids the need of having to again study the prosthesis, as well as testing the biocompatibility of the materials over a sufficiently long period. Thus, most rejections resulting from poor biocompatibility only appear after being implanted for several years.

SUMMARY OF THE INVENTION

The present invention relates to a high molecular weight polyolefin part, particularly for an articular prosthesis, whereof the structure has been modified by shaping in a closed mould, so as to improve the mechanical properties of the part, particularly its creep and wear resistance.

The production of thermoplastic material parts by shaping in a closed mould is a well known procedure used for many years for producing high density polyethylene and polypropylene parts. However, hitherto research carried out on the shaping of prostheses from thermoplastic materials has not made it possible to obtain, due to the choice of the shaping conditions a possible improvement in the mechanical characteristics of the parts.

Thus, hitherto the choice of the shaping conditions has mainly been studied with a view to obtaining parts free from defects from difficultly shapeable plastics materials, such as polyacetals, which have a limited ductility. This is more particularly described by K. M. KULKARNI in U.S. Pat. No. 3,825,648, which investigates the influence of certain shaping conditions on the quality of the parts obtained and deduces therefrom that one of the important parameters is the shaping speed which must not exceed a value closely linked with a complexity coefficient which more particularly takes account of the shape of the part to be produced. Thus, in this coefficient, the notion of the heterogeneity of the deformation does not appear and no improvement in the mechanical properties of the part is obtained by aiding certain local deformations.

However, other authors such as Paul Raymond Smith "Solid-phase forming polymers", March 1979, University of Leeds, PhD thesis have envisaged improving the mechanical properties of prostheses made from thermoplastic polymers, such as polyethylene, by the choice of certain shaping conditions. Thus, Smith has found that certain shaping conditions make it possible to improve the hardness of parts, but his experiments did not make it possible to obtain parts having improved wear and creep resistances compared with those of machined parts. However, it is known that creep is a very important phenomenon in estimating the long term strength of prostheses, because it is the main phenomenon in the evolution of the cup-shaped prosthesis.

The present invention specifically relates to a high molecular weight polyolefin part, particularly for an articular prosthesis, which has improved mechanical properties, particularly with regards to its creep and wear resistance, as well as to a process for the production of said part by shaping in a closed mould.

The high molecular weight polyolefin part according to the invention has a friction surface and is characterized in that the polyolefin structure is such that the polyolefin chains are oriented parallel to said friction surface, at least in the zone of said part located below or flush with said friction surface, so as to obtain a creep resistance after 48 hours equivalent to a deformation by creep of at the most 16% in the creep test according to ASTM standard D 695-80.

According to the invention, the term high molecular weight polyolefin is understood to mean a polyolefin such that a blank made therefrom and which has not undergone prior deformation retains its initial shape when raised to a temperature ranging from the melting point Tf of the polyolefin to approximately 10° C. above said melting point Tf. Generally, the polyolefin is polyethylene.

According to a preferred embodiment of the invention, the part is intended for an articular prosthesis, e.g. for a hip, knee or shoulder prosthesis.

This particular structure of the part according to the invention can be obtained during the production of said part by shaping in a closed mould, through the choice of certain shaping conditions, making it possible to control the local deformation rate or level of the polyolefin and thus obtain said orientation of the polyolefin chains, at least in the area of the part located below or flush with the friction surface.

Thus, the present invention relates to a process for the production of said part by shaping in a closed mould of a high molecular weight polyolefin blank.

This process comprises the following stages:

(a) heating to the shaping temperature a blank of said polyolefin, in which the blank length/transverse dimension ratio is between approximately 0.6 and approximately 1.7, the shaping temperature in the range between approximately 20° C. below the melting point Tf of said polyolefin and approximately 10° C. above said melting point Tf;

(b) placing the blank heated to the shaping temperature in a shaping mould which can be sealed by a punch displaceable in translation in said mould in the heightwise direction of the blank;

(c) applying to the punch a pressure exceeding the yield stress of said polyolefin at said shaping temperature and displacing said punch up to a final position for shaping said blank in said mould with a reduction rate of 0.4 to 0.8;

(d) maintaining the punch in the final position for a period between approximately 90 and approximately 150 seconds to obtain a homogeneous contraction and a good dimensional control of the final part; and (e) extracting the shaped part from the mould.

The choice, according to the invention, of the aforementioned shaping conditions makes it possible to obtain the desired deformation level, which constitutes the essential factor for improving the mechanical properties of the shaped part. Thus, the blank geometry, defined by the blank length/transverse dimension ratio is a vital factor involved in the definition of the local deformation rate of the material. According to the invention, use is made of a blank having a length/transverse dimension ratio of 0.6 to 1.7, because the deformations are greater when the length is high compared with the transverse dimension of the blank. However, it is not possible to exceed the value of 1.7, because beyond said value certain defects can be obtained, e.g. a poor sphericity of the friction surface in the case of a cup-shaped hip prosthesis. Moreover, for high values of the length/transverse dimension ratio, it is possible for there to be a buckling of the blank. At values below 0.6, the deformation level is not adequate to obtain an orientation of the polyolefin chains which is adequate for improving the creep resistance.

In order to obtain the desired deformation level under good conditions, the blank dimension must be adapted to the dimensions of the part to be produced. It is in particular preferable for the blank length to be such that the reduction rate obtained by shaping is 0.4. to 0.8. The reduction rate is defined by the formula:

$$\frac{h_i - H_f}{h_i}$$

In which $h_i$ is the blank length and $H_f$ the shaped part length and in the case of hip prostheses $H_f$ is the cup-shaped prosthesis thickness.

Other parameters such as the shaping temperature, the temperature of the mould and the shaping speed also influence the local deformation levels within the part. Thus, the shaping temperature to which the blank is raised constitutes an important parameter, because it is the main factor influencing the behaviour of the polyolefin. According to the invention, said shaping temperature is chosen in the range from 20° C. below the melting point Tf of said polyolefin and 10° C. above said melting point Tf.

It is pointed out that the melting point Tf of the polyolefin is determined by calorimetry and that it corresponds to the maximum calorimetrically recorded transformation speed. The melting of a polyolefin changes the mechanical behaviour thereof which passes from viscoelestoplastic to viscoelastic. This viscoelastic behaviour is observed in the melted state and the high viscosity of the high molecular weight polyolefin permits its transformation by shaping above the melting point. However, the orientation of the material is then less than in the case of shaping in the solid state. At low temperatures, i.e. at more than 20° C. below the melting point, polyolefin is fragile, so that fractures or breaks can appear therein. The best shaping temperature is consequently in the temperature range corresponding to the melting of the polyolefin and the carrying out of shaping at a temperature essentially corresponding to the end of melting, i.e. a good orientation of the polyolefin chains and few residual defects.

Moreover, the shaping temperature has a number of consequences on the shaped parts. Thus, the location of the deformation is highly dependent on the temperature of the blank, particularly when use is made of a punch at ambient temperature. Under these conditions a dead zone always appears and the deformation is transferred towards the inner zones of the part. In the case of a low blank temperature, the deformation occurs mainly in the vicinity of said dead zone, leaving the inner zones less oriented, whereas a higher temperature distributes the deformation over a greater thickness. In the latter case, the maximum local deformation rate is still not very high, but can be adequate. The shaping temperature also has an affect on the appearance and location of faults in the shaped part. Thus, these faults or defects are produced during to the withdrawal of the punch by elastic recovery of the polymer in accordance with Griffith's theory. During the elimination of the load, the elastic recovery of the polymer places the ends of the previously existing cracks under tension and leads to there extension in direction parallel to the surface. The greater the elastic contraction, the more pronounced this effect, i.e. at low temperatures.

In addition, a relatively low shaping temperature influences the defects:

(1) by localizing the deformation in the part, which leads to an increase in the maximum local deformation level, and (2) by increasing the elastic recovery of the polymer, which leads to the cracks becoming larger.

In the case of shaping parts in the form of cup shaped prostheses, the two cracking mechanisms lead to the development of holes in planes parallel to the inner surface of the prosthesis and the maximum deformation zones are essentially located at the bottom of the prosthesis. Therefore the appearance and development of these holes lead to a decohesion of the polymer and to a partial relaxation of the internal stresses. These two effects lead to a flattening of the bottom of the cup-shaped prosthesis where the holes are located as well as to sphericity defects. However, this effect which is relatively significant at relatively low temperatures becomes negligible at high temperatures. Moreover, the partial melting of the polyolefin is a major factor in the shaping process, because it greatly influences the properties and defects of the shaped part. In the process according to the invention, the blank is heated to the temperature chosen for shaping by heating in a preferably air-ventilated oven and the heating time is preferably 2 to 5 hours to obtain a good temperature uniformity in the blank.

The temperatures of the mould and/or punch can also play a part relative to the orientation of the polyolefin chains during shaping. Thus, on using a cold punch (at ambient temperature), there is a local lowering of the polyolefin temperature, whilst also increasing its modulus of elasticity and its yield stress. The cooled zone is no longer deformed and is consequently transformed into a dead zone. The deformation is transferred beyond said dead zone and the deformation rate of the grains and consequently the orientation of the polyolefin chains are increased. Thus, the choice of the punch temperature and the contact time between punch and blank depending on the shaping speed make it possible to control the thickness of the dead zone. However, a higher punch temperature makes it possible to eliminate the dead zone and in this case the deformation is at a maximum on the inner surface of the shaped part with which are associated faults oriented in the greatest extension direction of the polymer parallel to the surface.

According to the invention, the punch and/or mould temperatures can range between ambient temperature, e.g. approximately 20° C. and the shaping temperature and said temperatures are chosen as a function of the area of the part which it is wished to modify by orienting the polyolefin chains. Moreover, the punch and mould can be at different temperatures. When using a punch kept at a temperature below the shaping temperature, the shaping speed, i.e. the punch displacement speed, which determines the contact time between the punch and the blank during deformation, also constitutes an important parameter. Thus, it also determines the thickness of the dead zone and consequently the zones of the part where the polymer chains will be oriented.

The shaping speed also has an influence on the rheology of the polymer, but this phenomenon is less important. According to the invention, it is possible to use shaping speeds from 10 to 150 cm/min. Moreover, this speed can vary, if desired, during shaping, but it is preferable to remain within the aforementioned limits.

The time of maintaining the punch in the final position and the load applied thereto are also important parameters for the shaping process. Thus, polyolefins have a viscoelastoplastic behaviour and when a constant load is applied thereto, there can be a partial relaxation of the stresses within the polyolefin. These stresses are responsible for the elastic recovery during the removal of the load. Even in the case of a simple geometry, the distribution of the stresses and the orientation of the polyolefin chains are complex. It is then difficult to forecast the elastic recovery.

In the case of a cylindrical cavity, on varying the time during which the punch is maintained in the final position under maximum load, dimensional variations are obtained which can give a diabolo-shape geometry, when the maintenance time is short, or a barrel-shaped deformation when the maintenance time is long. Generally, the maintenance time under maximum load is at least 90 seconds and must not exceed approximately 150 seconds. Preferably, to obtain a homogeneous contraction of the polyolefin and a good dimensional control of the shaped parts, the maintenance time under maximum load is approximately 2 minutes.

The maximum load, i.e. the pressure applied to the punch must exceed the load necessary for completely filling the mould. This minimum value corresponds to the yield stress of the polyolefin at the shaping temperature. In the case of polyethylene, this yield stress is 2.5 MPa at 135° C. and a pressure of 10 to 80 MPa can be used for shaping.

The process according to the invention can in particular be used for producing cup-shaped prostheses for the hip. In this case, the displaceable punch can be a hemispherical punch, preferably associated with a cylindrical matrix having a hemispherical bottom facing the punch. Generally, the matrix and punch are made from steal or a light alloy.

BRIEF DESCRIPTION OF THE DRAWINGS

The invention is described in greater detail hereinafter relative to non-limitative embodiments and the attached drawings.

DETAILED DESCRIPTION OF THE PREFERRED EMBODIMENTS

Hereinafter a description is given of the process according to the invention for producing high molecular weight polyethylene cup-shaped hip prostheses with the following dimensions:

maximum external diameter: 49.7±0.2 mm,
internal diameter: 22.7±0.1 mm
thickness: 13.5±0.2 mm.

The blank which to undergo shaping is taken from a polyethylene sheet obtained by the compression and fritting of a polyethylene powder under the following conditions:

compacting under a pressure of 10 MPa at ambient temperature,
raising the temperature to 200° C. under a pressure of 1 MPa,
maintaining at 200° C. and then cooling to ambient temperature.

Figure 1:
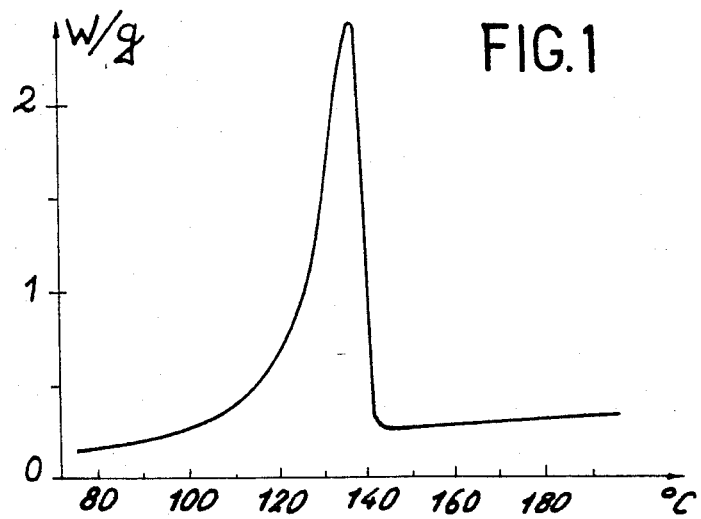
FIG. 1, is a graph for determining the melting point of the polyethylene used.
Figure 2A:
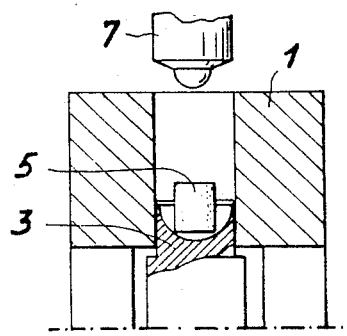
FIGS. 2a, 2b and 2c, diagrammatically and in vertical section show a closed mould shaping means used for the preparation of cup-shaped hip prostheses.

The polyethylene used is marketed under the reference HD 1000 by ERTA and the blank taken is cylindrical with a circular section, a length of 46 mm and a diameter of 28 mm. Polyethylene HD 1000 has the following characteristics:
mass density: 0.94 g/cm$^3$,
melting point: 135°–138° C.,
Shore hardness: d 65
elongation at break: >100% with a tractive speed of 125 mm/min;
tensile modulus: 650 MPa In order to choose the shaping temperature, it is firstly necessary to determine the melting point of this polyethylene by using a differential calorimetric analyzer with power compensation of the PERKIN ELMER DSC 2B type. The results obtained are given in FIG. 1, which is a graph showing the evolution of the specific heat as a function of the temperature. The melting peak is superimposed on the curve giving the specific heat evolution and it can be seen that the melting point corresponding to the maximum calorimetrically recorded transformation is 136° C. For shaping purposes, use is made of a hydraulic press with a maximum load of 10 tonne force. This press makes it possible to carry out shaping and maintain the maximum pressure for a sufficiently long time, which can exceed 10 min. It is equipped with a force transducer and a 10 min. It is equipped with a force transducer and a displacement transducer making it possible to record, during shaping, the force applied and also the displacement of the punch. The shaping speed can vary between 10 and 150 cm/min. For the production of cup-shaped prostheses, the punch used and which is shown in FIG. 2a is constructed in the following way.

Figure 2B:
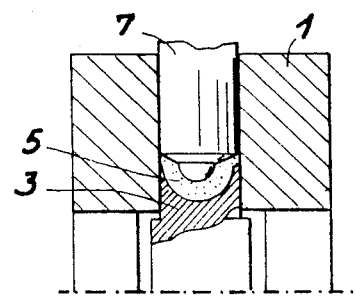
Figure 2C:
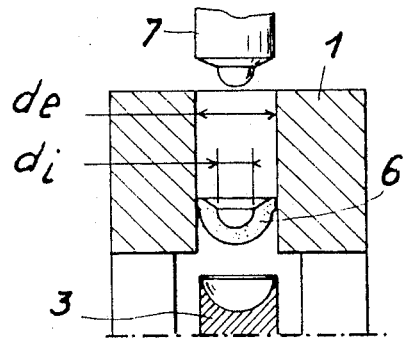

A metal belt 1, whereof the internal cylindrical portion has a diameter of 50 mm, an internal concave hemispherically shaped block 3 which supports the blank 5 at the start of shaping and which is detachable for facilitating the extraction of the shaped part, whereby the shaping force applied is measured under said member 3. The upper punch 7 is a convex hemispherical punch associated with a truncated cone for obtaining the internal shape of the cup-shaped prosthesis. It can move within the metal belt 1 at a constant speed until the mould is completely filled. The blank is firstly brought to the shaping temperature by heating it in an air ventilation oven at 140° C. for 5 hours, the blank being positioned vertically in contact with a controlled temperature conducting plate. Following said heating, it is introduced into the cavity of the shaping press, in the manner shown in FIG. 2a. The punch at a temperature of 20° C. is then moved until it comes into contact with the blank. A load of 9.8 tonne force (or a pressure of 50 MPa) is then applied to the punch and the latter is moved at a speed of 60 cm/min until the shaping mould cavity is completely filled by the blank and as shown in FIG. 2b. The punch 7 is maintained in this position under a maximum force of 9.8 tonne force for 2 minutes, followed by the withdrawal of punch 7 and the hemispherical block 3 in order to extract from the press the thus shaped part 6 and as shown in FIG. 2c.

This part has a good sphericity, is free from defects and has the following dimensions:
external diameter $d_e = 49.8$ mm,
internal diameter $d_i = 22.7 \pm 0.1$ mm.

This is followed by the determination of the orientation of the polymer chains in the thus obtained shaped part using optical examination. To this end, a sample is taken from the part by firstly cutting it into two using a saw along an axial plane and then cutting each half-part with the LEITZ 1515 microtome equipped with a steal knife to obtain sections with a thickness of 25 $\mu$m. These sections are then placed between two glass plates with an index liquid for reducing the refraction due to the cutting lines and they are observed by birefringence in linearly polarized natural light. This observation can be macroscopic over a complete section or microscopic with the aid of a polarizing microscope. It is thus possible to observe the directions of the main deformations which are the directions of the main optical indices and the values of the main deformations, which are dependent on the values of the main optical birefringences.

It is found that the polymer chains are oriented parallel to the internal surface of the cup-shaped prosthesis in the zone positioned slightly below the friction surface constituted by the concave hemispherical portion of the forged part.

Figure 3:
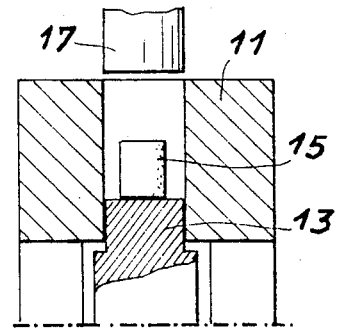
FIG. 3, diagrammatically shows another closed mould shaping configuration.

The following example illustrates the improvement, obtained as a result of the inventive process, to the wear and creep resistance of HD 1000 polyethylene parts shaped in the apparatus of FIG. 3. FIG. 3 shows that the shaping mould comprises a metal belt 11, whereof the cylindrical inner portion has a diameter of 50 mm, a flat lower block 13 supporting blank 15 and a flat cylindrical punch 17. As hereinbefore, the blanks are shaped under the following conditions:
shaping temperature: 140° C.,
temperature of punch 17: 20° C.,
shaping speed: 150 cm/min,
time during which punch is maintained in final position: 2 min,
dimensions of blanks: length 50 mm and diameter 33 mm.

This is followed by the checking of the wear and creep resistance of the shaped parts obtained, followed by the following tests:

(A) WEAR TEST

For this test use is made of a MARCELIN wear meter. The test pieces are extracted and machined from shaped parts, so as to test the polymer on the surfaces oriented parallel to the flow. These test pieces are in the form of washers with a thickness of $2 \pm 0.02$ mm and a diameter of $16 \pm 0.02$ mm cut parallel to the shaping direction. The following test conditions are used. Use is made of a cylindrical part of Z 100 C D17 steel, of diameter 30 mm and 0.1 $\mu$m $r_a$. The cylindrical shaft it is rotated at a speed of 150 rpm, or 0.4 m/s and a force of 0.5 kg force is applied for 192 hours. The measurements are performed under ambient conditions at a temperature of 22° C.

The evaluation of the wear is expressed by measuring the mean chord in millimeters of the wear notch caused. The results obtained are given in the following table 1, which also indicates the results obtained on HD 1000 polyethylene parts, which where not shaped.

TABLE 1

| unshaped HD 1000 polyethylene | shaped HD 1000 polyethylene |
|---|---|
| 2.77 | 2.46 |
| 2.7 | 2.45 |
| 2.85 | 2.41 |
| average: 2.77 | average: 2.44 |

(B) CREEP TEST

The tests where performed on a compression creep test machine according to ASTM standard D 695-80. The test pieces used where machined from parts shaped so as to be able to test the polymer in the same direction as the shaping. These test pieces are diameter 7 mm and height 10.5 mm cylinders cut parallel to the shaping direction. The following creep test conditions where used:
temperature: 20° C.,
nominal stress: 28.3 MPa,
test duration: 48 hours.
The results obtained are given in table 2, which also gives the results obtained on unshaped HD 1000 polyethylene samples.

TABLE 2

| polyethylene | instantaneous deformation | creep after 24 hours | creep after 48 hours |
|---|---|---|---|
| HD 1000 unshaped | 12.7% | 18.2% | 19.8% |
|  | 9.2% | 15.9% | 17.8% |
| HD 1000 shaped | 13.9% | 14.6% | 15.1% |
|  | 13.0% | 14.1% | 15.0% |

The results given in these two tables show that shaping made it possible to improve the wear and creep resistance properties of polyethylene parts as a result of the special shaping conditions.

What is claimed is:

1. A forging process for making a polyolefin part including an arcuate friction surface having improved creep and wear resistances comprising the steps of:
   (a) raising to the forging temperature a blank of high molecular weight polyolefin in which the blanks length/transverse dimension ratio is between approximately 0.6 and approximately 1.7, the forging temperature being in the temperature range from approximately 20° C. below the melting point Tf of said polyolefin and approximately 10° C. above said melting point Tf;
   (b) placing the blanks raised to the forging temperature in a forging mould which can be closed by a punch displaceable in translation in said mould in the lengthwise direction of the blank;
   (c) applying to the punch a pressure exceeding the yield stress of said polyolefin at said forging temperature and moving said punch to a final position for forging the blank in the mould with a reduction rate of 0.4 to 0.8 to provide a polyolefin part having an arcuate friction surface;
   (d) maintaining the punch in the final position for a period between approximately 90 and approximately 150 seconds; and
   (e) extracting the forged part from said mould.

2. A process according to claim 1, wherein the displaceable punch and/or mould are at a temperature between ambient temperature and the forging temperature.

3. A process according to claim 1, wherein the forging speed is 10 to 150 cm/minute.

4. A process according to claim 1, wherein the punch is maintained in the final position for a period of approximately 2 minutes.

5. A process according to claim 1, wherein the displaceable punch is a hemispherical punch.

6. A process according to claim 5, wherein the hemispherical punch is associated with a cylindrical mould having a hemispherical bottom facing the punch.

7. A process according to claim 1, wherein the mould is made from steel or light alloy.

8. A process according to claim 1, wherein the 8. A process according to claim 1, wherein the polyolefin is polyethylene.

9. A process according to claim 8, wherein the pressure applied to the displaceable punch is 10 to 80 MPa.

10. A process according to claim 1, wherein said punch has a hemispherical face for forging said arcuate friction surface with a corresponding hemispherical shape.

* * * * *